United States Patent
Hahn et al.

(10) Patent No.: US 9,464,112 B2
(45) Date of Patent: Oct. 11, 2016

(54) PEPTIDES HAVING NF-κB INHIBITORY ACTIVITY, OR COMPOSITION COMPRISING SAME

(71) Applicant: KNU-INDUSTRY COOPERATION FOUNDATION, Gangwon-do (KR)

(72) Inventors: Jang-Hee Hahn, Gangwon-do (KR); Chang-Seo Park, Gyeonggi-do (KR); In-Young Ko, Gangwon-do (KR); Byong-Ik Chun, Seoul (KR); Byoung-Chul Kim, Gangwon-do (KR)

(73) Assignee: KNU-INDUSTRY COOPERATION FOUNDATION, Gangwon-do (KR)

( * ) Notice: Subject to any disclaimer, the term of this patent is extended or adjusted under 35 U.S.C. 154(b) by 0 days.

(21) Appl. No.: 14/422,643

(22) PCT Filed: Aug. 20, 2013

(86) PCT No.: PCT/KR2013/007440
§ 371 (c)(1),
(2) Date: Feb. 19, 2015

(87) PCT Pub. No.: WO2014/030898
PCT Pub. Date: Feb. 27, 2014

(65) Prior Publication Data
US 2015/0252073 A1    Sep. 10, 2015

(30) Foreign Application Priority Data
Aug. 23, 2012  (KR) .................. 10-2012-0092400

(51) Int. Cl.
*A61K 38/06* (2006.01)
*A61K 38/07* (2006.01)
*A61K 8/64* (2006.01)
*A61Q 19/08* (2006.01)
*C07K 5/08* (2006.01)
*C07K 5/11* (2006.01)
*C07K 5/083* (2006.01)
*C07K 5/09* (2006.01)
*C07K 5/103* (2006.01)
*C07K 5/093* (2006.01)

(52) U.S. Cl.
CPC ............. *C07K 5/1019* (2013.01); *A61K 8/64* (2013.01); *A61K 38/06* (2013.01); *A61K 38/07* (2013.01); *A61Q 19/08* (2013.01); *C07K 5/0804* (2013.01); *C07K 5/0817* (2013.01); *C07K 5/0819* (2013.01); *C07K 5/101* (2013.01)

(58) Field of Classification Search
CPC ........ A61K 38/06; A61K 38/07; A61K 8/64; A61Q 19/08; C07K 5/08; C07K 5/0804; C07K 5/0817; C07K 5/0819; C07K 5/10; C07K 5/101; C07K 5/1019
USPC .................. 514/18.8, 21.9; 530/330, 331
See application file for complete search history.

(56) References Cited

U.S. PATENT DOCUMENTS

| | | | |
|---|---|---|---|
| 6,384,189 B1 * | 5/2002 | Murphy-Ullrich | C07K 5/1019 530/326 |
| 7,368,430 B2 | 5/2008 | Aggarwal et al. | |
| 2011/0059892 A1 | 3/2011 | Moussou | |
| 2012/0244575 A1 * | 9/2012 | Poth | C07K 14/415 435/68.1 |
| 2015/0337038 A1 * | 11/2015 | Korman | C07K 16/2827 424/142.1 |

OTHER PUBLICATIONS

SEQ ID No. 4295 from US 2012/0244575, p. 1. Sep. 2012.*
D'Acquisto et al "From willow bark to peptides: the ever widening spectrum of NF-κB inhibitors" Current Opinion in Pharmacology 2006, 6:387-392.
Gupta et al "Inhibiting NF-κB activation by small molecules as a therapeutic strategy" Biochimica et Biophysica Acta 1799 (2010) 775-787.
Nolan et al "DNA Binding and IKB Inhibition of the Cloned p65 Subunit of NF-KB, a rel-Related Polypeptide" Cell, vol. 64, 961-969, Mar. 6, 1991.
Sentandreu et al "Biochemical Properties of Dipeptidyl Peptidase III Purified from Porcine Skeletal Muscle" J. Agric. Food Chem. 1998, 46, 3977-3984.

* cited by examiner

*Primary Examiner* — Julie Ha
(74) *Attorney, Agent, or Firm* — Vorys, Sater, Seymour & Pease LLP; Mih Suhn Koh

(57) ABSTRACT

Provided are small peptide fragments derived from the NF-κB p65 subunit and a pharmaceutical or cosmetic composition comprising the same. The peptides have a NF-κB inhibitory activity, through controlling the transcription-activation of NF-κB. The peptides inhibit the expressions of pro-inflammatory mediators, which are induced by NF-κB, and also inhibit the transmigration of leukocytes, thereby exhibiting an anti-inflammatory activity. Especially, the peptides have excellent inhibitory activities against dermatitis and skin aging. And also, the peptides inhibit base membrane invasion of cancer cells, thereby exhibiting an inhibitory activity against the growth and/or metastasis of cancer cells.

7 Claims, 7 Drawing Sheets

PEPTIDES HAVING NF-κB INHIBITORY ACTIVITY, OR COMPOSITION COMPRISING SAME

The Sequence Listing submitted in text format (.txt) filed on Feb. 19, 2015, named "2-2_PN0128PCT_seq_list_text", created on Feb. 19, 2015, 905 bytes), is incorporated herein by reference.

TECHNICAL FIELD

The present invention relates to small peptide fragments having a NF-κB inhibitory activity and a composition comprising the same.

BACKGROUND ART

An inflammatory response is known as a protective response of living organism for rehabilitating the structures and functions of tissues damaged by infection, trauma, etc. Mobilization of leukocytes to a focus of inflammation is critical for the rapid resolution of infections and restoration of tissue damages resulting from a variety of injuries. However, a misdirected or prolonged inflammatory response causes damage to the body's tissues or diseases. For example, inflammatory diseases are caused by bacterial or viral infection, e.g., cerebrospinal meningitis, enteritis, dermatitis, uveitis, encephalitis, or adult respiratory distress syndrome, or non-infectious factors, e.g., trauma, autoimmune diseases, or organ transplantation rejection. Inflammatory diseases are classified into acute and chronic inflammatory diseases according to symptoms or pathological features. Acute inflammation such as allergy or bacterial/viral infection is manifested as local signs such as a change in bloodstream, blood vessel size, and vascular permeability, and the recruitment of leukocytes. In contrast, a main pathological feature of chronic inflammation such as rheumatoid arthritis, artheroscloerosis, chronic kidney infection, or hepatocirrhosis is a continuous emigration of macrophages, lymphocytes, or plasma cells into foci of inflammation due to recurrence of inflammatory factors, thereby causing a long-lasting inflammatory response.

Pro-inflammatory mediators expressed at the sites of inflammation, such as cytokines, chemokines, reactive oxygen intermediates, cycloxygenase-2 (COX-2), 5-lipoxygenase (5-LOX), matrix metalloproteinase (MMP), play a critical role in generation and maintenance of inflammatory reaction. It is known that the expressions of such pro-inflammatory mediators are controlled by transcription factors, such as NF-κB (nuclear factor κB), STAT3 (signal transducer and activator of transcription 3), AP-1 (activator protein1), HIF-1a (hypoxia-inducible factor 1a).

Cancer cells induced by carcinogens proliferate rapidly relative to normal cells, thereby forming tumor masses, invading surrounding tissues, and interfering with normal body functions. Cancer cells bring nutrients and oxygen by inducing angiogenesis, and metastasis thereof is also caused by angiogenesis. Although cancer cells grow infinitely at specific sites, they can also leave the sites from which they originated, migrate to and grow in new sites, whose process is called "metastasis". Metastasis involve several key steps: conversion of cancer cells to migratory mesenchymal cells, dissociation of the mesenchymal cells from the original tumor sites, invasion into and spread through surrounding connective tissues and capillary vessels, migration through blood vessels, escape from the blood vessels, migration through connective tissues, and proliferation in secondary sites.

Meanwhile, NF-κB has a homodimer form or a heterodimer form, which is derived from the 5 subunits, i.e., RelA (p65), c-Rel, RelB, p50 (NF-κB1), and p52 (NF-κB2). All the subunits share the DNA binding sites, the dimerization sites, the IκB (inhibitory KB) binding sites. In an inactivated state, NF-κB binds to IκB in the cytoplasm, which inhibits the translocation of NF-κB into the nucleus and the binding to target gene promoters. When NF-κB is activated by pro-inflammatory cytokines (e.g., TNFα, IL-1, etc.); physical stimuli (e.g., UV, radiation, etc.); pathogenic organisms and lipopolysaccharides (LPSs) derived therefrom; double-strand RNAs, etc., NF-κB dissociates from IκB to enter the nucleus and then binds to κB elements, thereby inducing the transcriptions of about 400 genes responsible for inflammation, immune response, tumor cell division, invasion, metastasis, angiogenesis, tolerance to anticancer agents, tolerance to radioactivity, etc. (Sethi G, Shanmugam M K, Ramachandrasn L, Kumar A P, Vinay Tergaonkar V. 2012. Multifaceted link between cancer and inflammation. *Biosci. Rep.* 32:1). Therefore, NF-κB is a transcription factor that plays a pivotal role in not only the control of pro-inflammatory cytokine expression but also the growth and/or metastasis of cancer cells.

DISCLOSURE

Technical Problem

The present inventors have performed various researches in order to develop small peptide fragments having a NF-κB inhibitory activity. The present inventors have found that the specific peptide fragments derived from a certain subunit (i.e., p65 subunit) of NF-κB control the transcription-activation of NF-κB, thereby being able to inhibit inflammatory reaction; and exhibit excellent inhibitory activities against dermatitis and skin aging that are closely related to the NF-κB mediated inflammation. And also, the present inventors have found that the specific peptide fragments inhibit angiogenesis and base membrane invasion of cancer cells, thereby inhibiting the growth and/or metastasis of cancer cells.

Therefore, it is an object of the present invention to provide the specific peptide fragments derived from the NF-κB p65 subunit.

It is another object of the present invention to provide a pharmaceutical composition having a NF-κB inhibitory activity, which comprises the specific peptide fragments as an active ingredient.

It is still another object of the present invention to provide a cosmetic composition for improving inflammation or skin aging, which comprises the specific peptide fragments as an active ingredient.

Technical Solution

In accordance with an aspect of the present invention, there is provided a peptide selected from the group consisting of the peptide of SEQ ID NO: 1, the peptide of SEQ ID NO: 2, the peptide of SEQ ID NO: 3 and the peptide of SEQ ID NO: 4.

In accordance with another aspect of the present invention, there is provided a pharmaceutical composition having a NF-κB inhibitory activity, which comprises a peptide selected from the group consisting of the peptide of SEQ ID NO: 1, the peptide of SEQ ID NO: 2, the peptide of SEQ ID NO: 3 and the peptide of SEQ ID NO: 4 as an active ingredient.

In an embodiment, the pharmaceutical composition having a NF-κB inhibitory activity may be a pharmaceutical composition for preventing or treating inflammation or skin aging. The inflammation may be dermatitis, preferably ultraviolet radiation-induced dermatitis. And also, the skin aging may be cutaneous photoaging, preferably ultraviolet radiation-induced cutaneous photoaging.

In another embodiment, the pharmaceutical composition having a NF-κB inhibitory activity may be a pharmaceutical composition for inhibiting the growth and/or metastasis of cancer cells. The cancer cells may be breast cancer cells, gastric cancer cells, colorectal cancer, colon cancer cells, rectal cancer cells, pancreatic cancer cells, or lymphoma cells.

In accordance with still another aspect of the present invention, there is provided a cosmetic composition for improving inflammation or skin aging, which comprises a peptide selected from the group consisting of the peptide of SEQ ID NO: 1, the peptide of SEQ ID NO: 2, the peptide of SEQ ID NO: 3 and the peptide of SEQ ID NO: 4 as an active ingredient. In the cosmetic composition of the present invention, the inflammation may be dermatitis, preferably ultraviolet radiation-induced dermatitis; and also, the skin aging may be is cutaneous photoaging, preferably ultraviolet radiation-induced cutaneous photoaging.

Advantageous Effects

It has been found by the present inventors that the specific peptide fragments derived from the NF-κB p65 subunit have a NF-κB inhibitory activity, through controlling the transcription-activation of NF-κB. Especially, it has been found by the present invention that the peptide fragments can inhibit inflammatory reaction; and exhibit excellent inhibitory activities against dermatitis and skin aging. Therefore, the peptides can be usefully applied to a pharmaceutical composition for preventing or treating inflammation or skin aging and a cosmetic composition for improving inflammation or skin aging. And also, the peptides inhibit angiogenesis and base membrane invasion of cancer cells, thereby being able to usefully apply to a pharmaceutical composition for inhibiting the growth and/or metastasis of cancer cells.

BEST MODE

Figure 1:
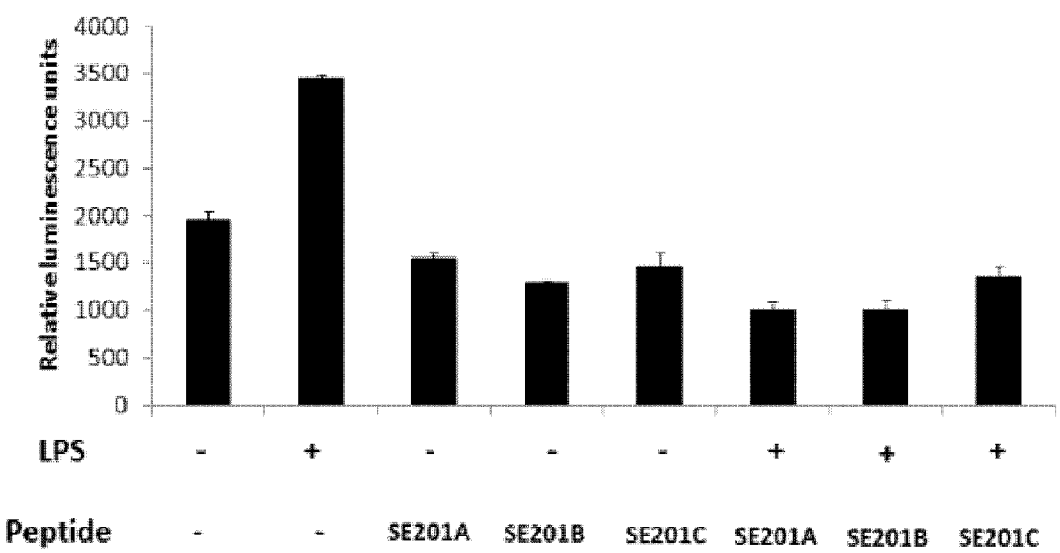
FIG. 1 shows the NF-κB activities in the mouse macrophage cell line RAW 264.7 transfected with the NF-κB reporter gene, after treatment with the peptides of the present invention.

Throughout the specification, the term "inflammation" refers to the inflammatory reaction whose expression is controlled by NF-κB (nuclear factor κB), including not only acute and/or chronic inflammatory diseases but also diseases involving inflammation (e.g., rheumatoid arthritis, osteoarthritis, etc.). The "inflammation" includes a NF-κB-mediated skin inflammation (i.e., dermatitis), preferably ultraviolet radiation-induced dermatitis, which may be derived from various causes.

The term "skin aging" refers to the skin aging caused by the transcription control by NF-κB and includes preferably cutaneous photoaging, more preferably ultraviolet radiation-induced cutaneous photoaging.

The present invention provides a peptide selected from the group consisting of the peptide of SEQ ID NO: 1, the peptide of SEQ ID NO: 2, the peptide of SEQ ID NO: 3 and the peptide of SEQ ID NO: 4.

The peptide selected from the group consisting of the peptide of SEQ ID NO: 1, the peptide of SEQ ID NO: 2, the peptide of SEQ ID NO: 3 and the peptide of SEQ ID NO: 4 have a NF-κB inhibitory activity, through controlling the transcription-activation of NF-κB. The peptides inhibit the expressions of various pro-inflammatory mediators that are induced by NF-κB; and the trans-endothelial migrations of leukocytes, thereby exhibiting an anti-inflammatory activity. Especially, the peptides exhibit excellent inhibitory activities against dermatitis and skin aging. And also, the peptides have an inhibitory activity against the growth and/or metastasis of cancer cells, through inhibiting angiogenesis and base membrane invasion of cancer cells.

Therefore, the present invention provides a pharmaceutical composition having a NF-κB inhibitory activity, which comprises a peptide selected from the group consisting of the peptide of SEQ ID NO: 1, the peptide of SEQ ID NO: 2, the peptide of SEQ ID NO: 3 and the peptide of SEQ ID NO: 4 as an active ingredient.

In an embodiment, the pharmaceutical composition having a NF-κB inhibitory activity may be a pharmaceutical composition for preventing or treating inflammation or skin aging. The inflammation may be dermatitis, preferably ultraviolet radiation-induced dermatitis. And also, the skin aging may be cutaneous photoaging, preferably ultraviolet radiation-induced cutaneous photoaging.

In another embodiment, the pharmaceutical composition having a NF-κB inhibitory activity may be a pharmaceutical composition for inhibiting the growth and/or metastasis of cancer cells. The cancer cells may be breast cancer cells, gastric cancer cells, colorectal cancer, colon cancer cells, rectal cancer cells, pancreatic cancer cells, or lymphoma cells.

The pharmaceutical composition of the present invention may include excipients such as lactose or corn starch, lubricants such as magnesium stearate, currently available emulsifiers, suspending agents, buffers, isotonic agents, etc. The pharmaceutical composition of the present invention can be administered in an oral or a parenteral dosage form, preferably in an external dosage form for applying on the skin. For intramuscular, intraperitoneal, subcutaneous, or intravenous administration, a sterilized solution of an active ingredient is generally prepared. In this case, the sterilized solution may include a buffer to achieve a desired pH value. With respect to formulations for intravenous administration, an isotonic agent may be used to render the formulations isotonic. The pharmaceutical compositions of the present invention can be formulated into aqueous solutions including a pharmaceutically acceptable carrier such as a saline of pH 7.4. The aqueous solutions can be introduced into a patient's intramuscular blood stream by local bolus injection. And also, the pharmaceutical composition of the present invention may be formulated to dosage forms for transdermal delivery, such as a solution for external use, an emulsion, an ointment, a patch, etc., according to conventional pharmaceutical processes. The pharmaceutical composition of the present invention can be administered to patients who suffer from various inflammatory diseases and cancers (such as breast cancer, gastric cancer, colorectal cancer, colon cancer, rectal cancer, pancreatic cancer, or lymphoma) at a daily dosage of about 1 to 2000 mg/kg. An adequate dosage is generally changed according to age, body weight, and conditions of a patient.

The present invention also provides a cosmetic composition for improving inflammation or skin aging, which comprises a peptide selected from the group consisting of the peptide of SEQ ID NO: 1, the peptide of SEQ ID NO: 2, the peptide of SEQ ID NO: 3 and the peptide of SEQ ID NO: 4 as an active ingredient. In the cosmetic composition of the present invention, the inflammation may be dermatitis, preferably ultraviolet radiation-induced dermatitis; and also, the skin aging may be is cutaneous photoaging, preferably ultraviolet radiation-induced cutaneous photoaging.

The cosmetic composition of the present invention may be in a functional cosmetic composition comprising the peptides as an active ingredient. The cosmetic composition may be prepared in various forms according to conventional methods thereof. For example, the cosmetic composition may be prepared in forms of cosmetic products, cosmetic solutions, creams, lotions, etc., which may be diluted with a cleansing water, an astringent solution, or a moisture solution, for the use thereof. And also, the cosmetic composition may include conventional excipients, such as a stabilizer, a solubilizing agent, vitamin, a pigment, a flavoring agent, which are conventionally used in the field of cosmetic composition. In the cosmetic composition, the peptide may be present in an amount enough to provide the effects for improving inflammation or skin aging, for example in an amount ranging from 0.001 to 10 weight %, preferably about 0.01 to 1 weight %, based on the total weight of the composition.

Hereinafter, the present invention will be described more specifically by the following examples and experimental examples. However, the following examples and experimental examples are provided only for illustrations and thus the present invention is not limited to or by them.

EXAMPLE 1

Synthesis of Peptides

The peptides of SEQ ID NOs: 1 to 4 were synthesized with an automatic peptide synthesizer (PeptrEx-R48, Peptron, Daejeon, Korea) using a FMOC solid-phase method. The synthesized peptides were purified and analyzed by reverse-phase high-performance liquid chromatography (reverse-phase HPLC) (Prominence LC-20AB, Shimadzu, Japan) using a C18 analytical RP column (Shiseido capcell pak), and isolated using a mass spectrometer (HP 1100 Series LC/MSD, Hewlett-Packard, Roseville, U.S.A.).

TABLE 1

| Peptide name | SEQ ID NO | Amino acid sequence |
|---|---|---|
| SE201A | SEQ ID NO: 1 | Arg-Phe-Arg |
| SE201B | SEQ ID NO: 2 | Leu-Lys-Ile-Cys |
| SE201C | SEQ ID NO: 3 | Lys-Ile-Cys-Arg |
| SE201D | SEQ ID NO: 4 | Asp-Val-His |

EXAMPLE 2

Preparation of Peptide-containing Compositions

The peptides of SEQ ID NOs: 1 to 4 were respectively dissolved in phosphate buffered saline (PBS) to a concentration of 1 M. The resultant protein solutions were also used in the following experimental examples.

EXPERIMENTAL EXAMPLE 1

Tests for Inhibition of NF-κB Activity in Macrophage

A reporter gene assay system was used for evaluating the activity of NF-κB. The reporter gene is a NF-κB-Luc in which several K enhancer elements (GGGAATTTC-CGGGAATTTCCGGGAATTTCCGGGAATTTC-CGGGAATTTCCGGGAA TTTCC) are bound to the firefly luciferase (Luc) gene derived from *Photinus pynalis* that is capable of binding with the NF-κB protein in cells. The NF-κB-Luc was purchased from Promega Corporation, USA) for the evaluation.

The macrophage cell line RAW264.7 (ATCC TIB-71, USA) was added to each well of a 12-well plate in the concentration of $2\times10^5$ cells. After 24 hours therefrom, NF-κB-Luc (0.25 mg/well) and the pCMV-LacZ plasmid (Clontech Co., USA) (0.1 mg/well) were co-transfected into the macrophage cell line RAW264.7, using the Fugene-6 transfection kit (Promega Co., USA), according to the vendor's instruction. After 12 hours therefrom, the cells were treated with the peptides of SEQ ID NOs: 1 to 3 in the concentration of 100 μM, respectively. After 30 minutes therefrom, the cells were treated with 10 ng/ml of lipopolysaccharide (LPS) and then cultured for 24 hours. Each reporter activity, i.e., NF-κB-Luc activity, was measured using the Dual™ Luciferase reporter assay system (Promega Corporation), according to the vendor's manual. The transduction efficiencies of the cells in each well were adjusted to the same level through the correction based on the β-galactosidase activity. All test results were verified through independent two separate experiments. The results obtained by measuring the NF-κB-Luc activities are shown in FIG. 1.

As shown in FIG. 1, the NF-κB-Luc activities in the groups treated with the peptides of SEQ ID NOs: 1 to 3 were significantly reduced (about 30~40% reduction). These results mean that the peptides of the present invention inhibit the synthesis of NF-κB-mediated pro-inflammatory cytokines.

EXPERIMENTAL EXAMPLE 2

Tests for Inhibitory Activity Against Trans-endothelial Migration of Monocytes

We evaluated the inhibitory activities of the peptides of the present invention on the trans-endothelial migration of leucocytes involving inflammatory reaction, using the mouse endothelial cell line bEnd.3 (ATCC CRL-2299, USA). The mouse endothelial cell line bEnd.3 ($4 \times 10^4$ cells) in Dulbecco's Modified Eagle medium (DMEM) supplemented with 10% serum were added to the upper compartments of Boyden chamber, and then cultured in a 5% $CO_2$ incubator at 37° C. for 24 hours. After washing with serum-free DMEM, the serum-free DMEM containing TNF-α (25 ng/ml) was added to each cell line, which was then cultured in a 5% $CO_2$ incubator at 37° C. for 4 hours. At this time, the peptides of SEQ ID NOs: 1 and 4 (100 μM) were also added to each test group. After the 4-hour culture, the mouse monocytes WEHI274.1 (ATCC CRL-1679, USA) ($1 \times 10^5$ cells) were added to each upper compartment of the chamber containing the bEND.3 cell line, and then the numbers of the monocytes migrated to each lower compartment were measured for 4 hours. At this time, an invasion-inducing medium (the supernatant isolated after culturing NIH 3T3 cells in serum-free DMEM containing 0.005% vitamin C and 0.1% bovine serum albumin for 24 hours) was placed in each lower compartment. The results thereof are shown in FIG. 2.

Figure 2:
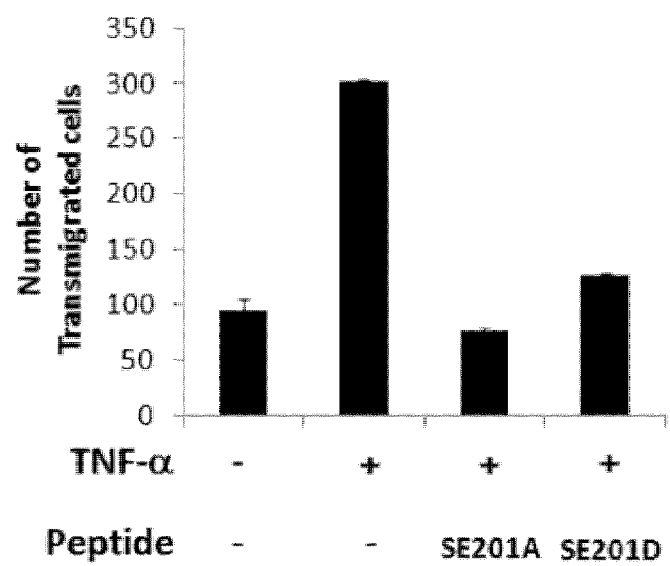
FIG. 2 shows the trans-endothelial migrations of WEHI274.1 cells, when the mouse endothelial cell line bEnd.3 activated by TNF-α was treated with the peptides of the present invention.

As shown in FIG. 2, trans-endothelial migrations of the monocytes in the groups treated with the peptides of SEQ ID NOs: 1 and 4 were significantly reduced (about 25~40% reduction) as compared with that in the control group. The peptides of SEQ ID NOs: 2 and 3 showed similar inhibitory effects (data not shown). Therefore, it is expected that the peptides according to the present invention inhibit the trans-endothelial migrations of leucocytes, thereby being able to inhibit inflammatory reaction.

EXPERIMENTAL EXAMPLE 3

Tests for Inhibitory Activity Against Tube Formation of Human Umbilical Vein Endothelial Cells (HUVECs)

Effects of the peptides of the present invention on angiogenesis were evaluated as follows.

Figure 3A:
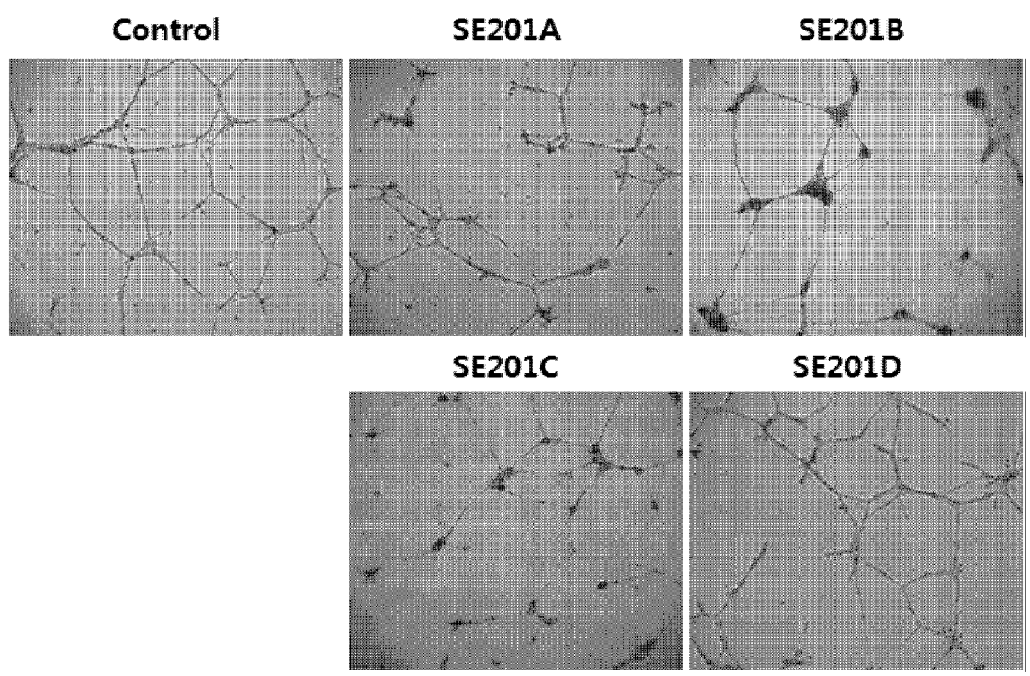
FIG. 3 shows the photographs obtained by observing tube formations when human umbilical vein endothelial cells (HUVECs) were treated with the peptides of the present invention (FIG. 3a); and the values obtained by the quantitative analyses for comparing the tube lengths thereof (FIG. 3b)
Figure 3B:
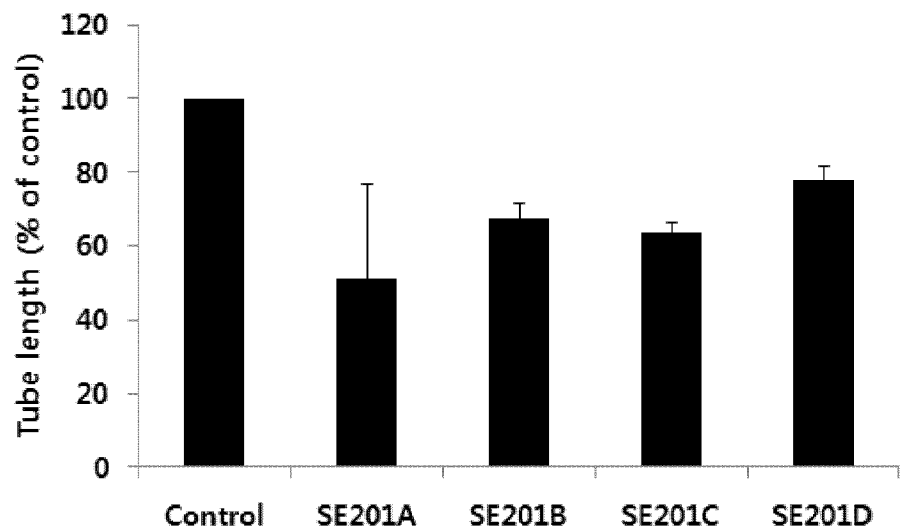

Generally, interactions of basement membrane components of blood vessels with vascular endothelial cells play an important role in formation and maintenance of new blood vessels. When matrigel, basement membrane components, is treated to 24-well culture plate, plugs are formed through polymerization reaction. HUVECs were seeded at a density of $8 \times 10^4$ cells/well to each well of the 24-well culture plate coated with matrigel. The protein solutions including each peptide of SEQ ID NOs: 1 to 4 (3 μg/Ml) prepared as in Example 2 and bFGF (basic fibroblast growth factor, 150 ng/Ml) were added to the wells. After incubation for 24 hours, formation of new blood vessels was examined using an inverted microscope (at 50× magnification). The photographs obtained by observing tube formations are shown in FIG. 3a. The values obtained by the quantitative analyses for comparing the tube lengths thereof are shown in FIG. 3b. In FIGS. 3a and 3b, the control is a group treated with only PBS having no peptide.

As shown in FIGS. 3a and 3b, it can be seen that, when treated with the peptides of the present invention, tube formations thereof were significantly reduced.

EXPERIMENTAL EXAMPLE 4

Evaluation of the Expressions of Procollagen Type-1 and MMP-1 in Human Dermal Fibroblasts It is known that MMP-1, the expression of which is induced by ultraviolet stimulation in human dermal fibroblasts, degrades collagen fibers to facilitate cutaneous photoaging as well as wrinkle formation. Since the expression of MMP-1 is induced by NF-κB activation, we evaluate the inhibition thereof by the treatment of the peptides of the present invention, using human dermal fibroblasts (ATCC PCS-201-012, USA).

Figure 4:
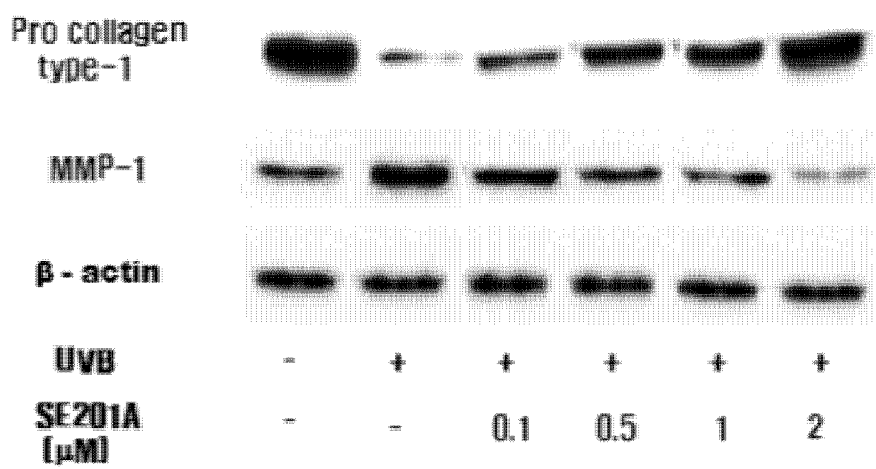
FIG. 4 shows the results obtained by evaluating the expressions of procollagen type-1 and MMP-1 in human dermal fibroblasts, after treatment with the peptides of the present invention.

The human dermal fibroblasts was irradiated with UVB (312 nm, 12.5 mJ/cm$^2$) and then treated with the peptide of SEQ ID NO: 1 in the concentrations of 0.1~2 μM. After 48 hours, the cell extracts were subject to the Western blotting assay so as to measure the expressions of MMP-1 and procollagen type-1. The results thereof are shown in FIG. 4. As shown in FIG. 4., the expression of MMP-1 increased by ultraviolet stimulation was reduced according to the treatment of the peptide of SEQ ID NO: 1 in dose-dependent manner; and the expression of procollagen type-1 increased by ultraviolet stimulation was increased according to the treatment of the peptide of SEQ ID NO: 1 in dose-dependent manner. Therefore, it can be seen that the peptide of the present invention can inhibit ultraviolet radiation-induced cutaneous photoaging.

EXPERIMENTAL EXAMPLE 5

Analysis of Pro-inflammatory Factors in Human Keratinocytes HaCaT

Figure 5:
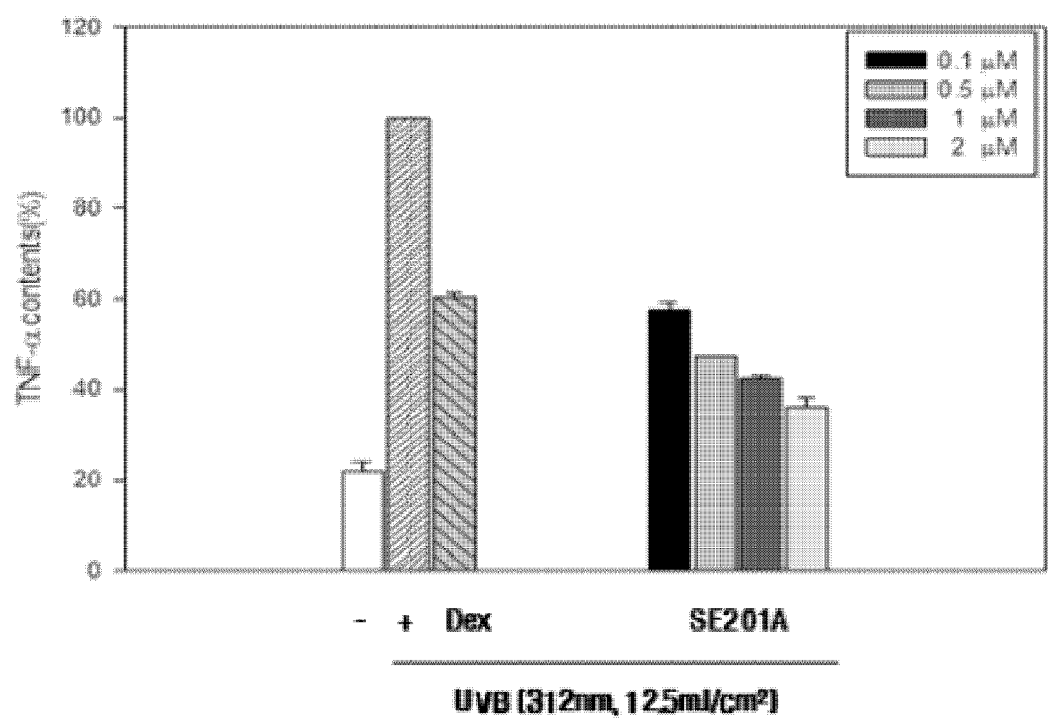
FIG. 5 shows the results obtained by evaluating the expression of TNF-α in human keratinocytes, after treatment with the peptides of the present invention.
Figure 6:
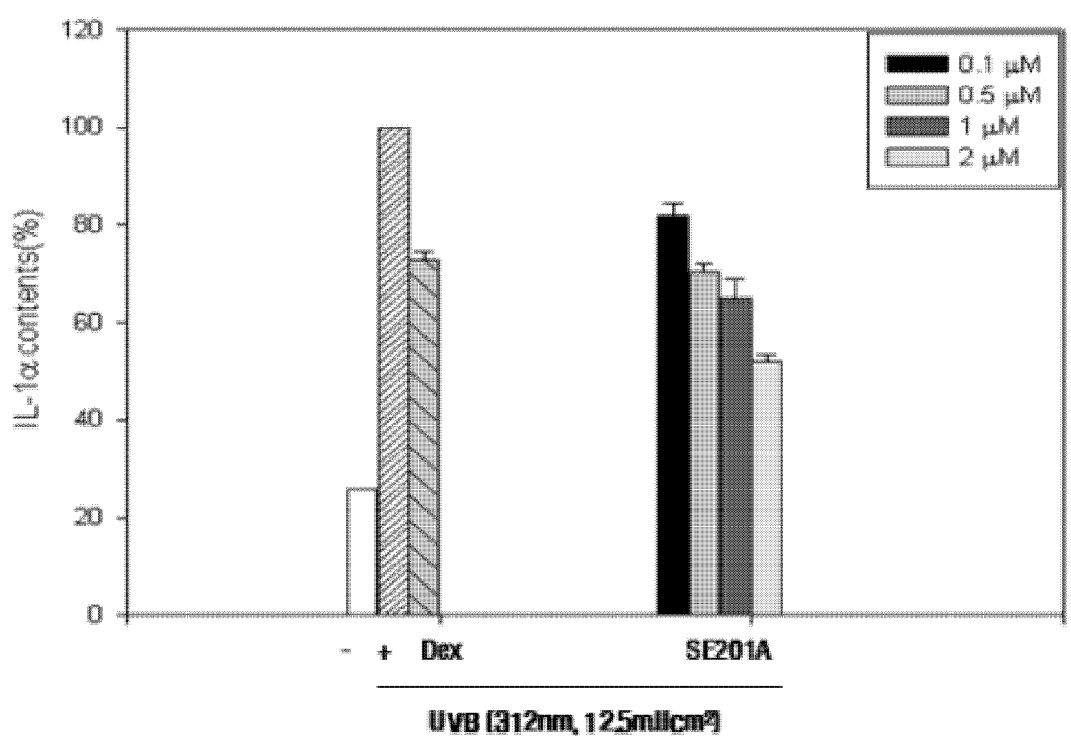
FIG. 6 shows the results obtained by evaluating the expression of IL-1α in human keratinocytes, after treatment with the peptides of the present invention.

We evaluated the inhibitory activities of the peptide of the present invention on expressions of the representative pro-inflammatory factors, i.e., TNF-α and IL-1α, the expressions of which are induced by ultraviolet stimulation. Specifically, the HaCaT cells (Molecular Biology Engineering Lab, Chemical & Biochemical Engineering, Dongguk University) were irradiated with UVB (312 nm, 12.5 mJ/cm$^2$) and then treated with the peptide of SEQ ID NO: 1 in the concentrations of 0.1~2 μM. At this time, the control group was treated with dexamethasone (Dex) having the immunosuppressive function, at the irradiation of UVB. After 48 hours, the cell extracts were subject to the Western blotting assay so as to measure the expressions of TNF-α and IL-1α. The results thereof are shown in FIGS. 5 and 6. As shown in FIGS. 5 and 6, the expressions of TNF-α and IL-1α were reduced in the control group treated with dexamethasone; and also in the test group treated with the peptide of SEQ ID NO: 1 in dose-dependent manner.

Figure 7:
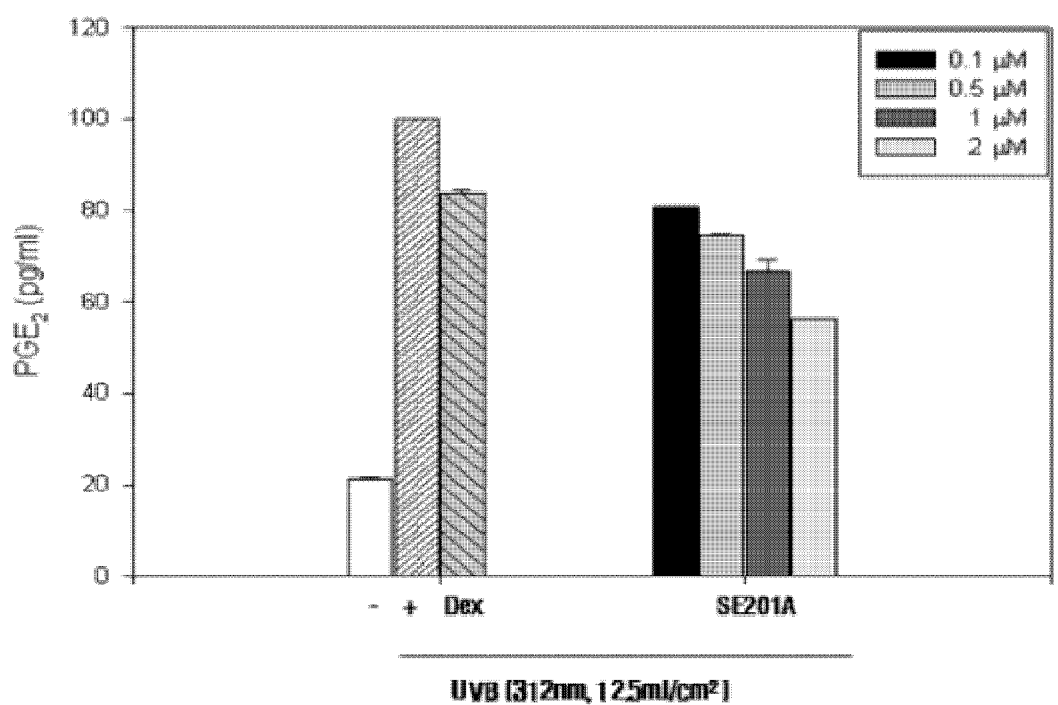
FIG. 7 shows the results obtained by evaluating the inhibitory effects of the peptides of the present invention on $PGE_2$ formation in human keratinocytes.
Figure 8:
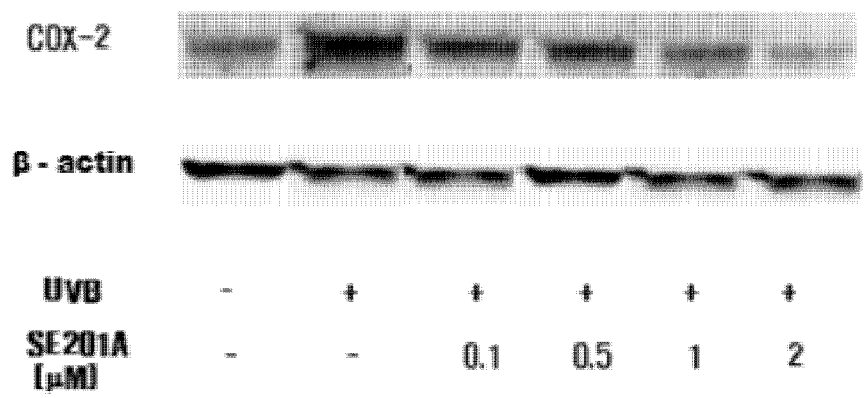
FIG. 8 shows the results obtained by evaluating the inhibitory effects of the peptides of the present invention on COX-2 formation in human keratinocytes.

And also, the cell extracts were subject to the enzyme immunoassay so as to evaluate the inhibitory effects on formation of $PGE_2$ (one of pro-inflammatory factors). The results thereof are shown in FIG. 7. For this assay, we also used the group treated with dexamethasone at the irradiation of UVB as a control group. In addition, the expression of COX-2 (which is a $PGE_2$ formation-mediating enzyme) was measured through the Western blotting assay; and the results thereof are shown in FIG. 8. As shown in FIGS. 7 and 8, the $PGE_2$ formation increased by ultraviolet stimulation was reduced according to the treatment of the peptide of SEQ ID NO: 1 in dose-dependent manner; and the expression of COX-2 was also reduced according to the treatment of the peptide of SEQ ID NO: 1 in dose-dependent manner. Therefore, it can be seen that the peptide of the present invention can effectively inhibit ultraviolet radiation-induced inflammation.

EXPERIMENTAL EXAMPLE 6

Tests for Inhibitory Activity Against Invasion of Cancer Cells

After matrigel, basement membrane components, is subject to polymerization reaction in a transwell, human breast cancer cells MCF-7 ($2 \times 10^5$ cells) were loaded to the upper compartment of the transwell and then treated with each peptide of SEQ ID NOs: 1 and 4 in the concentration of 100 µM, along with 0.1% BSA. An invasion-inducing medium (the supernatant isolated after culturing NIH 3T3 cells in serum-free DMEM containing 0.005% vitamin C and 0.1% bovine serum albumin for 24 hours) was placed in each lower compartment. The cells were cultured in a 5% $CO_2$ incubator at 37° C. for 12 hours. Cells migrated into the lower compartments of the transwell were counted three times at 24-hour intervals, and then the results were statistically analyzed. The control is a group treated with only PBS having no peptide. The results thereof are shown in FIG. 9.

Figure 9:
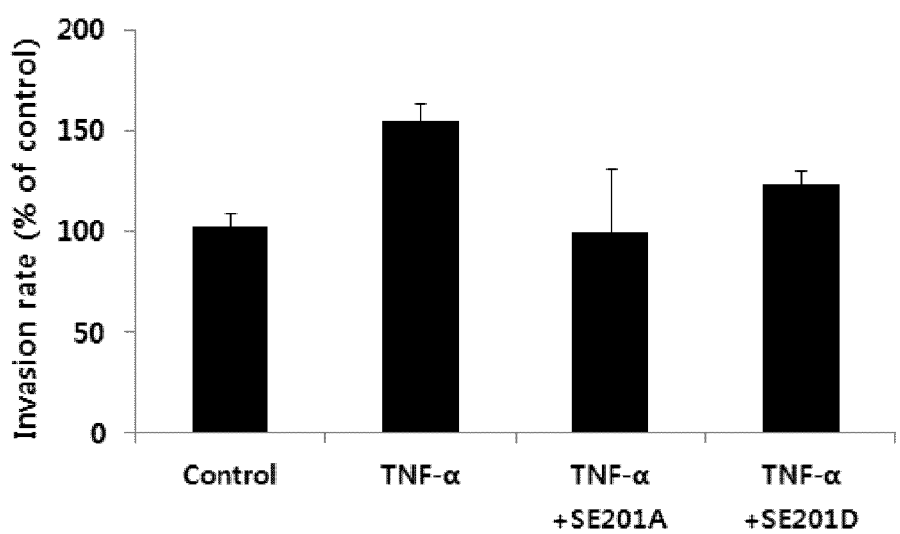
FIG. 9 shows the results obtained by measuring the invasion of human breast carcinoma cells (MCF-7) into matrigel, after treatment with the peptides of the present invention.

As shown in FIG. 9, in the groups treated with the peptides of SEQ ID NOs: 1 and 4 of the present invention, the base membrane invasion rates of the human breast cancer cells were reduced by about 60% to 80% relative to that of the control group with no peptide-treatment. Taking into consideration that cancer cells come out from blood vessels and invade basement membranes or surrounding connective tissues and then spread to secondary sites, it can be seen that peptides of the present invention can effectively inhibit the metastasis of cancer cells.

---

The invention claimed is:

1. A peptide inhibiting NF-κB activity as set forth in SEQ ID NO: 4.

2. A method for improving inflammation or skin aging through inhibiting activity of NF-κB in a subject, comprising administering a cosmetically effective amount of a peptide derived from the NF-κB p65 subunit, the peptide being selected from the group consisting of the peptide of SEQ ID NO: 1 and the peptide of SEQ ID NO: 4.

3. The method according to claim 2, wherein the inflammation is dermatitis.

4. The method according to claim 3, wherein the inflammation is ultraviolet radiation-induced dermatitis.

5. The method according to claim 2, wherein the skin aging is cutaneous photoaging.

6. The method according to claim 5, wherein the skin aging is ultraviolet radiation-induced cutaneous photoaging.

7. A method for inhibiting activity of NF-κB in a subject, comprising administering a cosmetically effective amount of a peptide derived from the NF-κB p65 subunit, the peptide being selected from the group consisting of the peptide of SEQ ID NO: 1 and the peptide of SEQ ID NO: 4.

* * * * *

SEQUENCE LISTING

```
<160> NUMBER OF SEQ ID NOS: 4

<210> SEQ ID NO 1
<211> LENGTH: 3
<212> TYPE: PRT
<213> ORGANISM: Artificial Sequence
<220> FEATURE:
<223> OTHER INFORMATION: Peptide fragment

<400> SEQUENCE: 1

Arg Phe Arg
  1

<210> SEQ ID NO 2
<211> LENGTH: 4
<212> TYPE: PRT
<213> ORGANISM: Artificial Sequence
<220> FEATURE:
<223> OTHER INFORMATION: Peptide fragment

<400> SEQUENCE: 2

Leu Lys Ile Cys
  1

<210> SEQ ID NO 3
<211> LENGTH: 4
<212> TYPE: PRT
<213> ORGANISM: Artificial Sequence
<220> FEATURE:
<223> OTHER INFORMATION: Peptide fragment

<400> SEQUENCE: 3

Lys Ile Cys Arg
  1

<210> SEQ ID NO 4
<211> LENGTH: 3
<212> TYPE: PRT
<213> ORGANISM: Artificial Sequence
<220> FEATURE:
```

-continued

```
<223> OTHER INFORMATION: Peptide fragment

<400> SEQUENCE: 4

Asp Val His
1
```